US 8,265,369 B2

(12) United States Patent
Crucs

(10) Patent No.: US 8,265,369 B2
(45) Date of Patent: Sep. 11, 2012

(54) APPARATUS AND METHOD FOR VIRTUAL FLAW REMOVAL FROM X-RAY SENSITIVE PLATES

(75) Inventor: Kevin M. Crucs, Copley, OH (US)

(73) Assignee: Apteryx, Inc., Akron, OH (US)

( * ) Notice: Subject to any disclaimer, the term of this patent is extended or adjusted under 35 U.S.C. 154(b) by 610 days.

(21) Appl. No.: 12/425,028

(22) Filed: Apr. 16, 2009

(65) Prior Publication Data

US 2010/0266187 A1     Oct. 21, 2010

(51) Int. Cl.
  *G06K 9/00*     (2006.01)
(52) U.S. Cl. .............................................. 382/132
(58) Field of Classification Search .............. 382/132
  See application file for complete search history.

(56) References Cited

U.S. PATENT DOCUMENTS

| | | | |
|---|---|---|---|
| 4,498,005 A | 2/1985 | Oono et al. | |
| 5,072,119 A | 12/1991 | Yamaguchi | |
| 5,164,993 A * | 11/1992 | Capozzi et al. ............... | 382/132 |
| 5,264,684 A | 11/1993 | Weil | |
| 5,334,851 A | 8/1994 | Good et al. | |
| 5,376,806 A | 12/1994 | Hejazi | |
| 5,418,355 A | 5/1995 | Weil | |
| 5,434,418 A | 7/1995 | Schick | |
| 5,592,374 A | 1/1997 | Fellegara et al. | |
| 5,712,890 A * | 1/1998 | Spivey et al. ............... | 378/37 |
| 5,832,055 A * | 11/1998 | Dewaele ............... | 378/62 |
| 5,995,583 A | 11/1999 | Schick et al. | |
| 6,249,596 B1 | 6/2001 | Buytaert et al. | |
| 6,356,652 B1 | 3/2002 | Vuylsteke | |
| 6,457,861 B1 * | 10/2002 | Petrick et al. ............... | 378/207 |
| 6,529,618 B1 | 3/2003 | Ohara et al. | |
| 6,542,575 B1 * | 4/2003 | Schubert et al. ............... | 378/98.4 |
| 6,763,084 B2 | 7/2004 | Boehm et al. | |
| 6,864,917 B2 | 3/2005 | Malloy Desormeaux | |
| 6,896,539 B2 | 5/2005 | Dobbs et al. | |
| 7,034,873 B2 * | 4/2006 | Mendis et al. ............... | 348/246 |
| 7,072,443 B2 | 7/2006 | Schick et al. | |
| 7,136,454 B2 * | 11/2006 | Gerndt et al. ............... | 378/98.12 |
| 7,182,021 B2 | 2/2007 | Maehashi | |
| 7,193,219 B2 | 3/2007 | Schick et al. | |
| 7,194,064 B2 | 3/2007 | Razzano et al. | |
| 7,210,847 B2 | 5/2007 | Hack | |
| 7,245,697 B2 | 7/2007 | Lang | |
| 7,281,847 B2 | 10/2007 | Kokkaliaris et al. | |
| 7,289,132 B1 | 10/2007 | Reid et al. | |

(Continued)

OTHER PUBLICATIONS

Tortajada, et al., Image Correction and Reconstruction for Breast Biopsy, E.A. Krupinski (Ed.): IWDM 2008, LNCS 5116, pp. 545-552, 2008.*

*Primary Examiner* — Rodney Fuller
(74) *Attorney, Agent, or Firm* — Hahn Loeser & Parks LLP

(57) ABSTRACT

A system, a method, and computer readable media for generating a corrected image from image information extracted from an X-ray sensitive plate. First, flaw map image information is extracted from an X-ray sensitive plate in order to determine any flaws (e.g., scratches) on the plate. Then the plate is exposed to capture physical image information (e.g., anatomical information) and the physical image information is extracted from the plate. The flaw map information is used to identify corresponding flaws in the extracted physical image information. Image processing is performed to correct the flaws (e.g., due to scratches on the X-ray sensitive plate) in the physical image information to form a corrected physical image.

31 Claims, 13 Drawing Sheets

U.S. PATENT DOCUMENTS

| | | |
|---|---|---|
| 7,289,601 B2 * | 10/2007 | Caseault et al. ............. 378/98.3 |
| 7,319,234 B2 * | 1/2008 | Kanegae ....................... 250/587 |
| 7,362,916 B2 | 4/2008 | Yamazaki |
| 7,580,589 B2 * | 8/2009 | Bosco et al. .................. 382/275 |
| 7,639,849 B2 * | 12/2009 | Kimpe et al. ................. 382/128 |
| 2001/0009454 A1 | 7/2001 | Manico et al. |
| 2002/0129488 A1 | 9/2002 | Lieberman |
| 2004/0169149 A1 | 9/2004 | Alzner et al. |
| 2005/0036692 A1 | 2/2005 | Iida et al. |
| 2005/0098619 A1 | 5/2005 | Ito et al. |
| 2005/0117031 A1 | 6/2005 | Russon et al. |
| 2005/0195214 A1 | 9/2005 | Reid et al. |
| 2006/0064639 A1 | 3/2006 | Reid et al. |
| 2006/0066453 A1 | 3/2006 | Homanfar et al. |
| 2006/0257816 A1 | 11/2006 | Klemola et al. |
| 2007/0018125 A1 | 1/2007 | Fletcher-Heath et al. |
| 2009/0040364 A1 * | 2/2009 | Rubner ......................... 348/362 |

* cited by examiner

FIG. 9
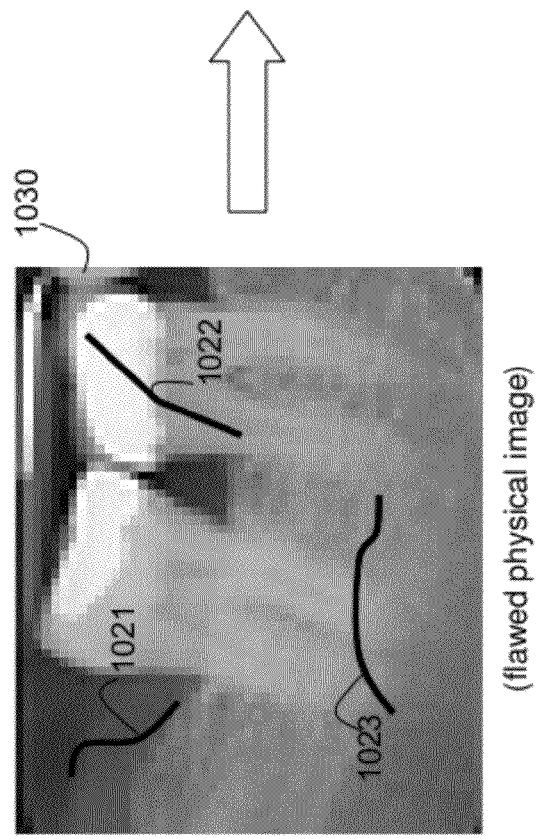
(flawed physical image)
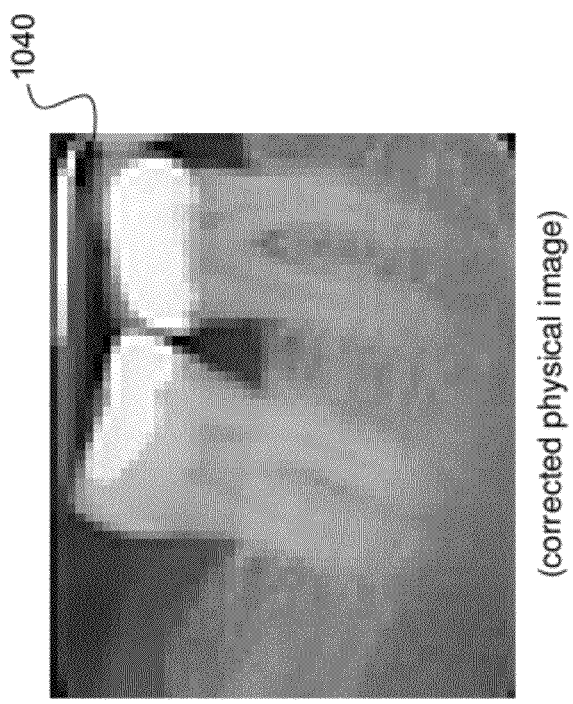
(corrected physical image)

APPARATUS AND METHOD FOR VIRTUAL FLAW REMOVAL FROM X-RAY SENSITIVE PLATES

TECHNICAL FIELD

Certain embodiments relate to digital radiography. More particularly, certain embodiments relate to virtual flaw removal from X-ray sensitive plates by correcting flaws in resultant images caused by flaws in the X-ray sensitive plates.

BACKGROUND

Various types of imaging systems are available for imaging the surface and/or the interior of such diverse entities such as, for example, the human anatomy, animals, man-made physical structures such as welding joints in bridges, geological formations, bodies of water, as well as many others. For example, in the field of dentistry, various types of intra-oral sensors exist which are used for capturing images of the inside of teeth and surrounding anatomy (e.g., bone structure) by exposing the anatomy and sensors to X-ray radiation. Such imaging techniques are well known using such intra-oral sensors as, for example, X-ray sensitive phosphor plates. Such X-ray sensitive phosphor plates can become damaged or scratched during, for example, normal use, resulting in such scratches or flaws appearing in images created using the X-ray sensitive phosphor plates.

Further limitations and disadvantages of conventional, traditional, and proposed approaches will become apparent to one of skill in the art, through comparison of such systems and methods with the subject matter of the present application as set forth in the remainder of the present application with reference to the drawings.

SUMMARY

A system, a method, and computer readable media for generating a corrected image from image information extracted from an X-ray sensitive plate (e.g., an X-ray sensitive phosphor plate) are disclosed. First, flaw map image information is extracted from an X-ray sensitive plate in order to determine any flaws (e.g., scratches) on the plate. Then the plate is exposed to capture physical image information (e.g., anatomical information) and the physical image information is extracted from the plate. The flaw map information is used to identify corresponding flaws in the extracted physical image information. Image processing is performed to correct the flaws (e.g., due to scratches on the X-ray sensitive plate) in the physical image information to form a corrected physical image. Extracting flaw map image information and identifying flaws may be a recurring process that is performed periodically for a particular plate in order to keep the flaw map information up to date (i.e., being representative of the current flaws in the plate).

A first embodiment of the present invention comprises a method to generate a corrected image from image information extracted from an X-ray sensitive plate. The method includes generating flaw map image data using an X-ray sensitive plate and generating physical image data using the X-ray sensitive plate. The method further includes identifying flawed pixel locations within the flaw map image data using a computer-based platform. The method also includes correlating pixel locations within the physical image data with identified flawed pixel locations within the flaw map image data using the computer-based platform. The method further includes correcting the correlated pixel locations within the physical image data using the computer-based platform to generate a corrected physical image.

The method may further include reporting a level of degradation of the X-ray sensitive plate based on the identified flawed pixel locations using the computer-based platform. The method may also include tracking a number of times that the X-ray sensitive plate is used to generate the physical image data using the computer-based platform.

Generating flaw map image data using the X-ray sensitive plate may include uniformly flooding the X-ray sensitive plate with X-ray radiation using an X-ray source, reading the X-ray sensitive plate using a scanning apparatus to extract the flaw map image data, reading an identifying code on the X-ray sensitive plate using a code reading device, and storing the flaw map image data in the computer-based platform and associating the flaw map image data with the identifying code within the computer-based platform. In accordance with an alternative embodiment of the present invention, instead of directly radiating the X-ray sensitive plate, a phantom plate may be positioned between the X-ray source and the X-ray sensitive plate. Such a phantom plate may serve to uniformly attenuate the X-ray radiation to a desired lower exposure level or to project a known pattern onto the X-ray sensitive plate.

In accordance with a further alternative embodiment of the present invention, instead of having an identifying code on the X-ray sensitive plate, the X-ray sensitive plate may include a form of memory (e.g., a relatively small memory chip or magnetic dots) for storing the flaw map image data. The memory on the X-ray sensitive plate is capable of being written to and read from using, for example, a laser scanning technique or a magnetic reading technique. Other memory writing and reading techniques are possible as well.

Generating physical image data using the X-ray sensitive plate may include capturing a physical representation on the X-ray sensitive plate using an X-ray source, reading the X-ray sensitive plate using a scanning apparatus to generate physical image data, reading an identifying code on the X-ray sensitive plate using a code reading device, and storing the physical image data in the computer-based platform and associating the physical image data with the identifying code within the computer-based platform.

The step of identifying flawed pixel locations within the flaw map image data may include applying an image analysis algorithm to the flaw map image data using the computer-based platform. The step of correlating pixel locations within the physical image data with the identified flawed pixel locations within the flaw map image data may include applying an image alignment algorithm to align the flaw map image data with the physical image data using the computer-based platform. The step of correcting the correlated pixel locations within the physical image data to generate a corrected physical image may include applying an image processing algorithm to the physical image data using the computer-based platform.

The identifying code may be implemented on the X-ray sensitive plate via one of radio frequency identification (RFID) technology, optical encoding technology, magnetic encoding technology, and bar coding technology. Other technologies may be possible as well.

Another embodiment of the present invention comprises a system to generate a corrected image from image information extracted from an X-ray sensitive plate. The system includes means for generating flaw map image data using an X-ray sensitive plate, means for generating physical image data using the X-ray sensitive plate, means for identifying flawed pixel locations within the flaw map image data, means for correlating pixel locations within the physical image data with the identified flawed pixel locations within the flaw map image data, and means for correcting the correlated pixel locations within the physical image data to generate a corrected physical image.

The system may further include means for reporting a level of degradation of the X-ray sensitive plate based on the identified flawed pixel locations. The system may also include means for tracking a number of times that the X-ray sensitive plate is used to generate the physical image data.

The means for generating flaw map image data using an X-ray sensitive plate may include means for uniformly flooding the X-ray sensitive plate with X-ray radiation, means for reading the X-ray sensitive plate to extract the flaw map image data, means for reading an identifying code on the X-ray sensitive plate, and means for storing the flaw map image data and associating the flaw map image data with the identifying code.

The means for generating physical image data using the X-ray sensitive plate may include means for capturing a physical representation on the X-ray sensitive plate, means for reading the X-ray sensitive plate to generate physical image data, means for reading an identifying code on the X-ray sensitive plate, and means for storing the physical image data and associating the physical image data with the identifying code.

The means for identifying flawed pixel locations within the flaw map image data may include means for performing image analysis on the flaw map image data. The means for correlating pixel locations within the physical image data with the identified flawed pixel locations within the flaw map image data may include means for aligning the flaw map image data with the physical image data. The means for correcting the correlated pixel locations within the physical image data to generate a corrected physical image may include means for image processing the physical image data.

The identifying code may be implemented on the X-ray sensitive plate via one of radio frequency identification (RFID) means, optical encoding means, magnetic encoding means, and bar coding means. Other technologies may be possible as well.

A further embodiment of the present invention comprises computer readable media having computer readable instructions recorded thereon for generating a corrected image from image information extracted from an X-ray sensitive plate. The instructions include instructions for identifying flawed pixel locations within flaw map image data extracted from an X-ray sensitive plate, instructions for correlating pixel locations within physical image data extracted from the X-ray sensitive plate with the identified flawed pixel locations within the flaw map image data, and instructions for correcting the correlated pixel locations within the physical image data to generate a corrected physical image.

The instructions for identifying flawed pixel locations within the flaw map image data may include instructions for applying an image analysis algorithm to the flaw map image data. The instructions for correlating pixel locations within the physical image data with the identified flawed pixel locations within the flaw map image data may include instructions for applying an image alignment algorithm to align the flaw map image data with the physical image data. The instructions for correcting the correlated pixel locations within the physical image data to generate a corrected physical image may include instructions for applying an image processing algorithm to the physical image data.

The computer readable media may further include instructions for associating the flaw map image data with the physical image data based on a common identifying code. The computer readable media may also include instructions for reporting a level of degradation of the X-ray sensitive plate based on the identified flawed pixel locations. The computer readable media may further include instructions for tracking a number of times that the X-ray sensitive plate is used to generate the physical image data. The computer readable media may include, for example, computer electronic memory, a compact disk (CD), a flash memory card, a hard drive, or any other type of computer readable media.

These and other novel features of the subject matter of the present application, as well as details of illustrated embodiments thereof, will be more fully understood from the following description and drawings.

BRIEF DESCRIPTION OF THE DRAWINGS

FIG. 9 illustrates an example embodiment of a process of generating a flawless or corrected physical image from flawed physical image data using the flaw map image data;

DETAILED DESCRIPTION

The following description is presented in the context of intra-oral imaging for the field of dentistry. However, various embodiments may be applied to other imaging fields as well such as, for example, other branches of medical imaging. Furthermore, the following description is presented in the context of using X-ray sensitive phosphor plates. However, the various embodiments may apply to other types of X-ray sensitive technologies as well that currently exist or do not yet exist.

Figure 1:
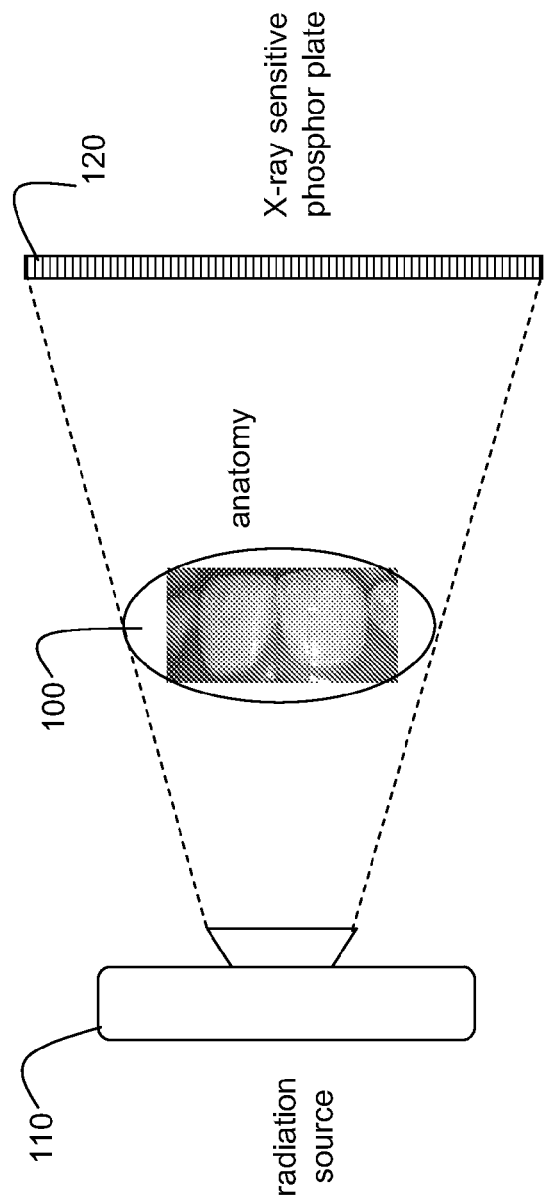
FIG. 1 illustrates a schematic diagram of an example embodiment of a process for capturing an image of a physical structure using a radiation source and an X-ray sensitive phosphor plate.

FIG. 1 illustrates a schematic diagram of an example embodiment of a process for capturing an image of a physical structure 100 using a radiation source 110 (e.g., an X-ray tube) and an X-ray sensitive phosphor plate 120 (a.k.a., a photostimulable phosphor plate) which are well known in the art. Radiation sources may include various types of X-ray machines. The X-ray tube 110 emits a dose of X-ray radiation toward the physical structure 100 (e.g., teeth of a patient). Some of the X-ray radiation passes through the physical structure 100 and exposes the X-ray sensitive phosphor plate 120, capturing an image of the physical structure 100 on the image medium 120.

Figure 2:
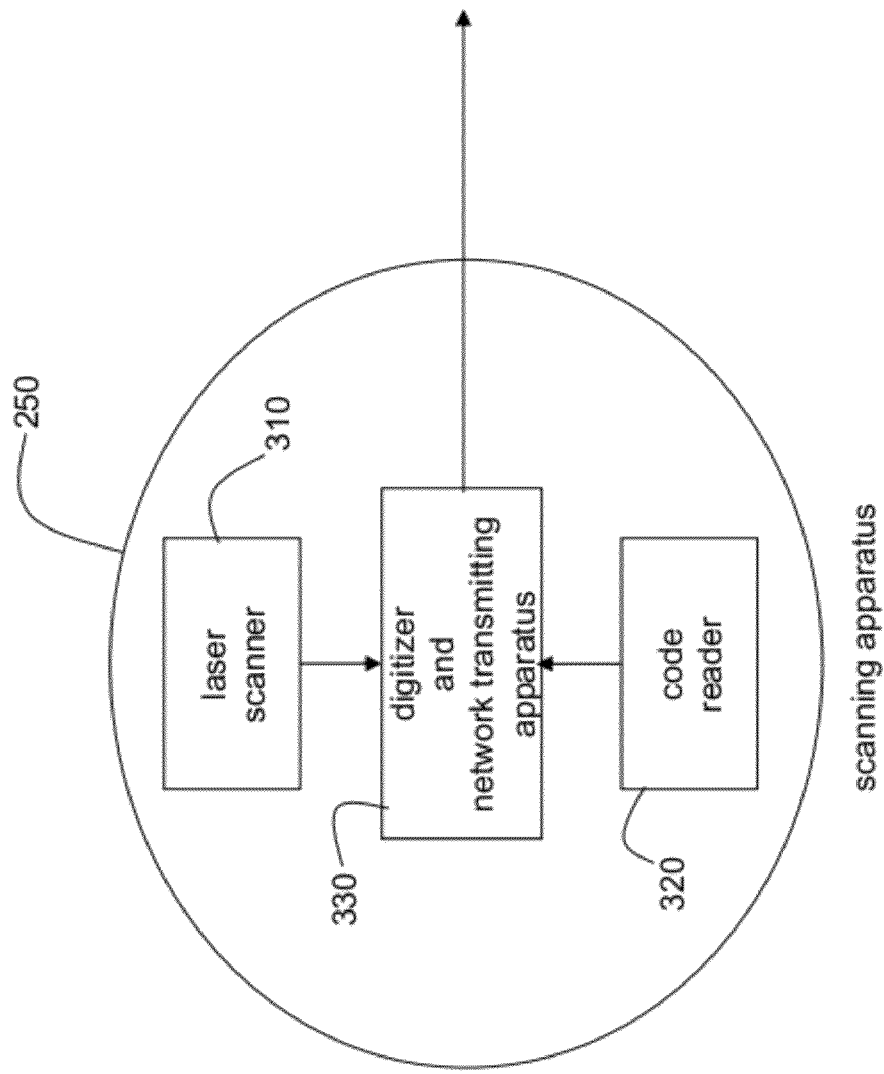
FIG. 2 illustrates a schematic block diagram of an example embodiment of a scanning apparatus.

FIG. 2 illustrates a schematic block diagram of an example embodiment of a scanning apparatus 250. The scanning apparatus 250 is capable of scanning the X-ray sensitive phosphor plate to digitally extract a captured image from the X-ray sensitive phosphor plate using a laser scanner 310. Furthermore, in accordance with an embodiment, each X-ray sensitive phosphor plate is encoded with an identifying code and the scanning apparatus 250 is capable of reading the identifying code of any X-ray sensitive phosphor plate using a code reading device 320. Such capabilities are explained in further detail later herein. In accordance with an embodiment of the present invention, one unique identifying code is associated with each particular X-ray sensitive phosphor plate.

In accordance with a further alternative embodiment of the present invention, instead of having an identifying code on the X-ray sensitive plate, the X-ray sensitive plate may include a form of memory (e.g., a relatively small memory chip or magnetic dots) for storing the flaw map image data. The memory on the X-ray sensitive plate is capable of being written to and read from using, for example, a laser scanning technique or a magnetic reading technique. Other memory writing and reading techniques are possible as well.

In accordance with still another alternative embodiment of the present invention, instead of having an identifying code on the X-ray sensitive plate, the identification of the X-ray sensitive plate may be determined by the size and/or shape of the X-ray sensitive plate, or by extracting flaw map image data from the X-ray sensitive plate and matching that flaw map image data to flaw map image data that was previously extracted from the X-ray sensitive plate. Other means of identification of an X-ray sensitive plate may be possible as well.

The scanning apparatus 250 also includes a digitizer and network transmitting apparatus 330 which is operationally connected to the laser scanner 310 and the code reading device 320. The laser scanner 310 is capable of scanning an image from an X-ray sensitive phosphor plate 120 to extract a digital image. The laser scanner 310 may be configured to scan a photostimulable phosphor plate (see FIG. 3) in accordance with various embodiments. Also, the code reading device 320 is capable of reading an identifying code on an X-ray sensitive phosphor plate. The code reading device 320 may be configured as an RFID reader, an optical reader, a magnetic reader, or a bar code reader in accordance with various embodiments. Other types of readers may be possible as well, in accordance with various embodiments. A user places an X-ray sensitive phosphor plate 120 into the scanning apparatus 250 to have both the exposed image and the identifying code read by the laser scanner 310 and the code reading device 320, respectively.

Figure 3:
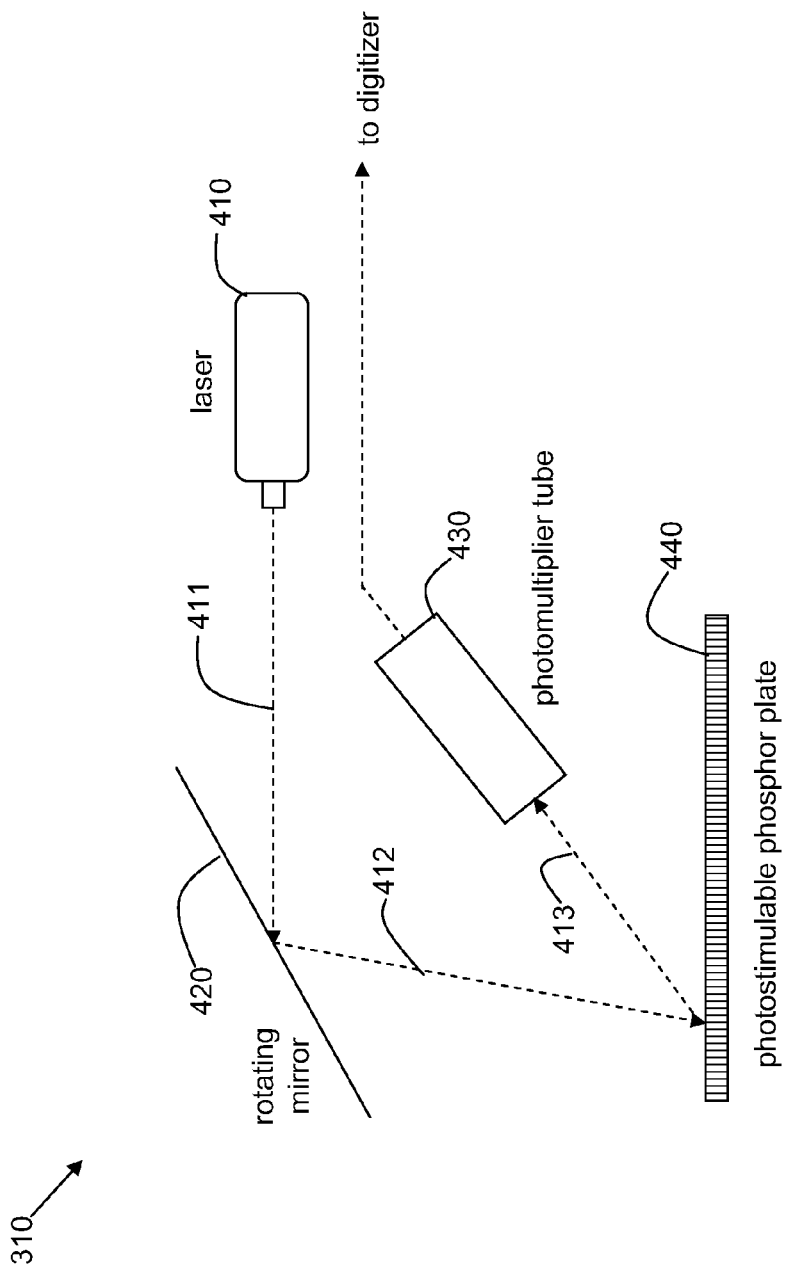
FIG. 3 illustrates a schematic block diagram of a first example embodiment of the laser scanner of FIG. 2.

FIG. 3 illustrates a schematic block diagram of a first example embodiment of the laser scanner 310 of FIG. 2. The laser scanner 310 includes a laser source 410, a rotating mirror 420, and a photomultiplier tube 430. When scanning a photostimulable phosphor plate 440, the laser source 410 emits a laser beam 411 toward the rotating mirror 420 which reflects the laser beam toward the photostimulable phosphor plate 440. The reflected laser beam 412 interacts with the photostimulable phosphor plate 440 causing light 413, representative of image pixels, to be directed toward the photomultiplier tube 430. As the mirror 420 rotates, the entire exposed surface of the photostimulable phosphor plate 440 is illuminated and scanned in this manner to extract all of the associated image pixels. The photomultiplier tube 430 amplifies the light associated with the image pixels as scanning proceeds and converts the light to analog electrical signals. The analog electrical signals may then be passed on to a digitizer 330 operationally connected to an output of the photomultiplier tube 430 to convert the analog electrical signals to digital electrical signals, to form digital pixel image data. Such a digitizer may be part of the laser scanner 310, or may be part of the digitizer and network transmitting apparatus 330, in accordance with various embodiments. Such laser scanners are well known in the art.

Figure 4:
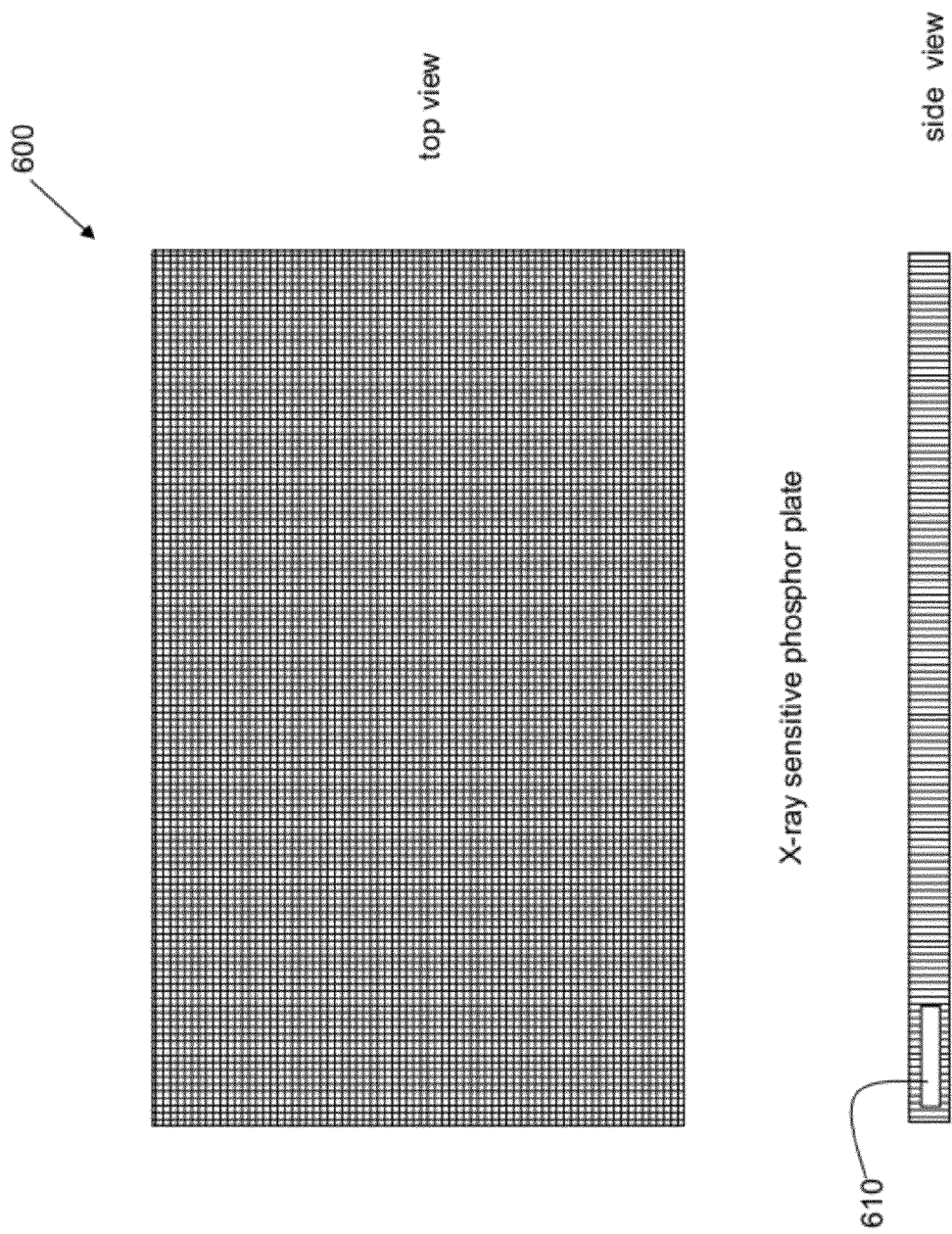
FIG. 4 illustrates a schematic diagram of an example embodiment of an X-ray sensitive phosphor plate having an RFID tag encoded with an identifying code.
Figure 5:
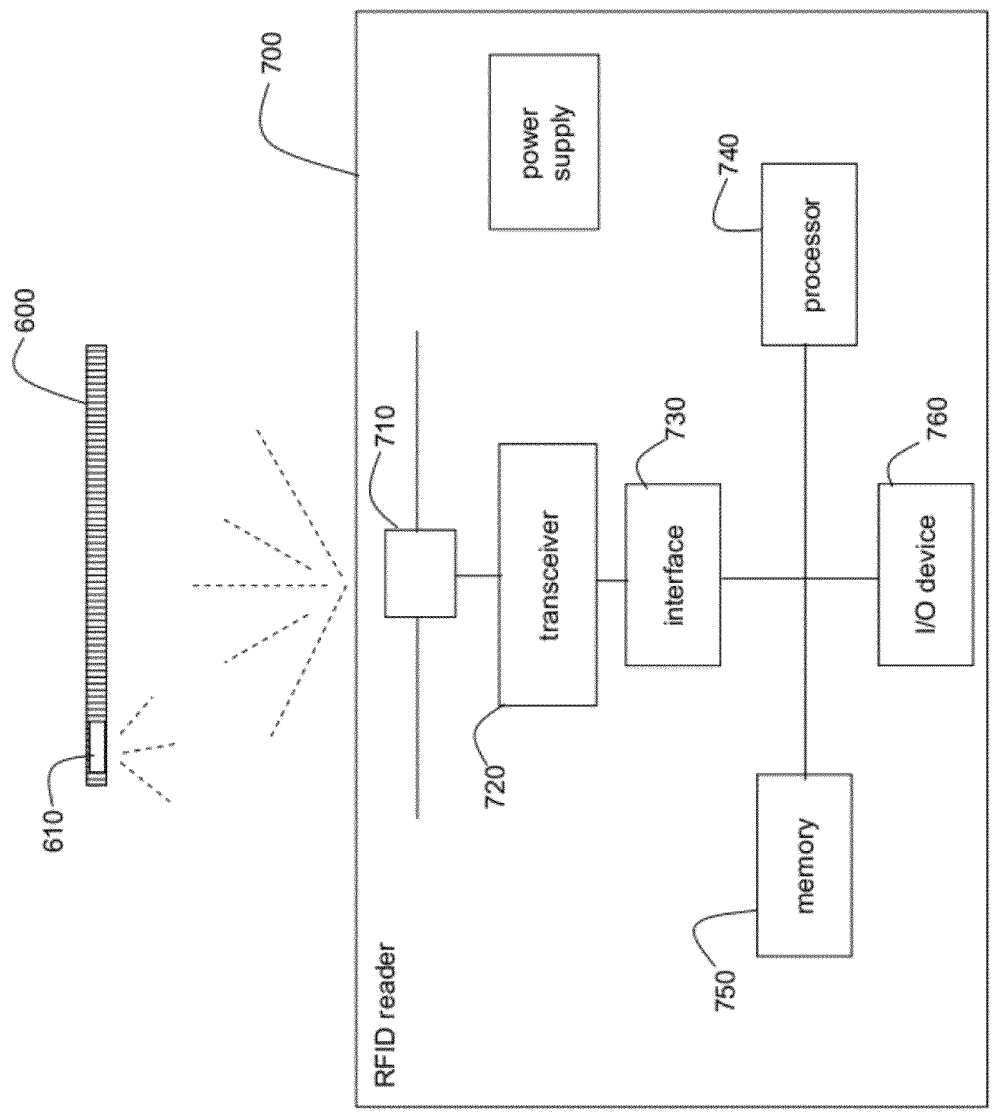
FIG. 5 illustrates a schematic block diagram of an example embodiment of the code reading device of FIG. 2 as being an RFID reader, and an example embodiment of a process for reading the RFID tag of the X-ray sensitive phosphor plate of FIG. 4.

FIG. 4 illustrates a schematic diagram of an example embodiment of an X-ray sensitive phosphor plate 600 having an RFID tag 610 encoded with an identifying code. FIG. 5 illustrates a schematic block diagram of an example embodiment of the code reading device 320 of FIG. 2 as being an RFID reader 700, and an example embodiment of a process for reading the RFID tag 610 of the X-ray sensitive phosphor plate 600 of FIG. 4.

The RFID reader 700 includes an antenna 710 and a transceiver 720 operationally connected to the antenna 710. The RFID reader 700 further includes an interface 730 operationally connected to the transceiver 720. The interface 730 may serve, at least in part, as a signal sampling unit and an A/D converter, for example. The RFID reader also includes a processor 740, a memory 750, and an input/output (I/O) device 760 operationally connected to each other and to the interface 730. The RFID reader 700 also includes a power supply 770 to supply power to the various elements of the RFID reader 700. Such RFID readers are well known in the art.

When an X-ray sensitive phosphor plate 600 (i.e., a photostimulable phosphor plate) having an encoded RFID tag is placed into the scanning apparatus 250. The code reading device 320 (being the RFID reader 700) interrogates the RFID tag 610 via an RF energy signal generated by the transceiver 720 and transmitted toward the RFID tag 610 via the antenna 710. Upon receiving the RF energy signal, the RFID tag 610 responds by transmitting back an RF energy signal representative of the identifying code encoded in the RFID tag 610. The transceiver 720 of the RFID reader 700 receives the RF signal from the RFID tag 610 via the antenna 710 and the processor 740 processes the signal to form the digital identifying code which may be stored in memory 750 and/or forwarded to the digital processing and network transmitting apparatus 330 of the scanning apparatus 250 as the identifying code of the X-ray sensitive phosphor plate 600.

Figure 6:
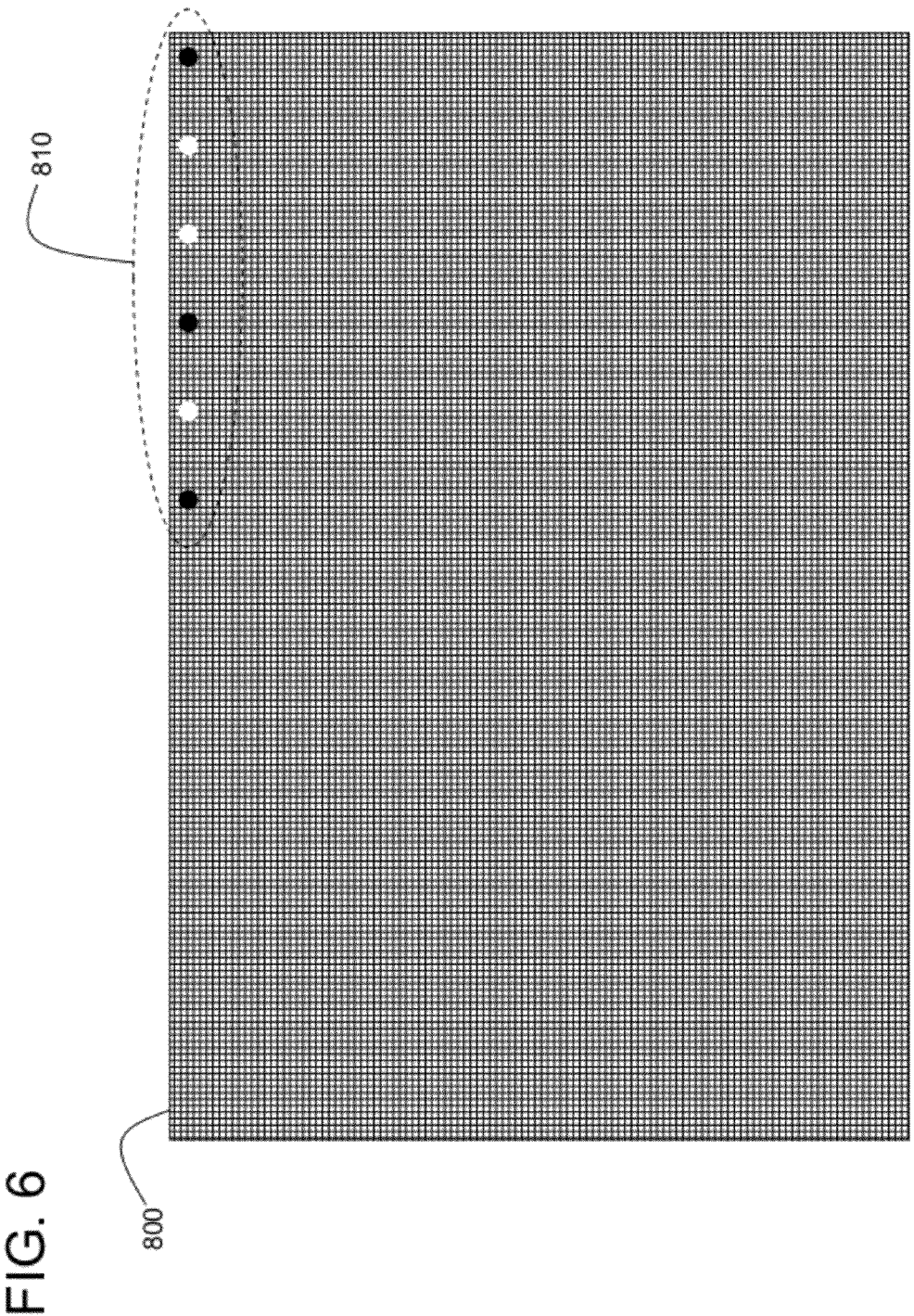
FIG. 6 illustrates a schematic diagram of an example embodiment of an X-ray sensitive phosphor plate having an optical code encoding an identifying code.

FIG. 6 illustrates a schematic diagram of an example embodiment of an X-ray sensitive phosphor plate 800 having an optical code 810 encoding an identifying code. The optical code 810 is formed by open holes and filled holes along the edge of the X-ray sensitive phosphor plate 800. For example, the open and filled holes 810 shown in FIG. 6 represent the digital code "010110" as read from left to right, where an open hole represents a "1" and a filled hole represents a "0".

Figure 7:
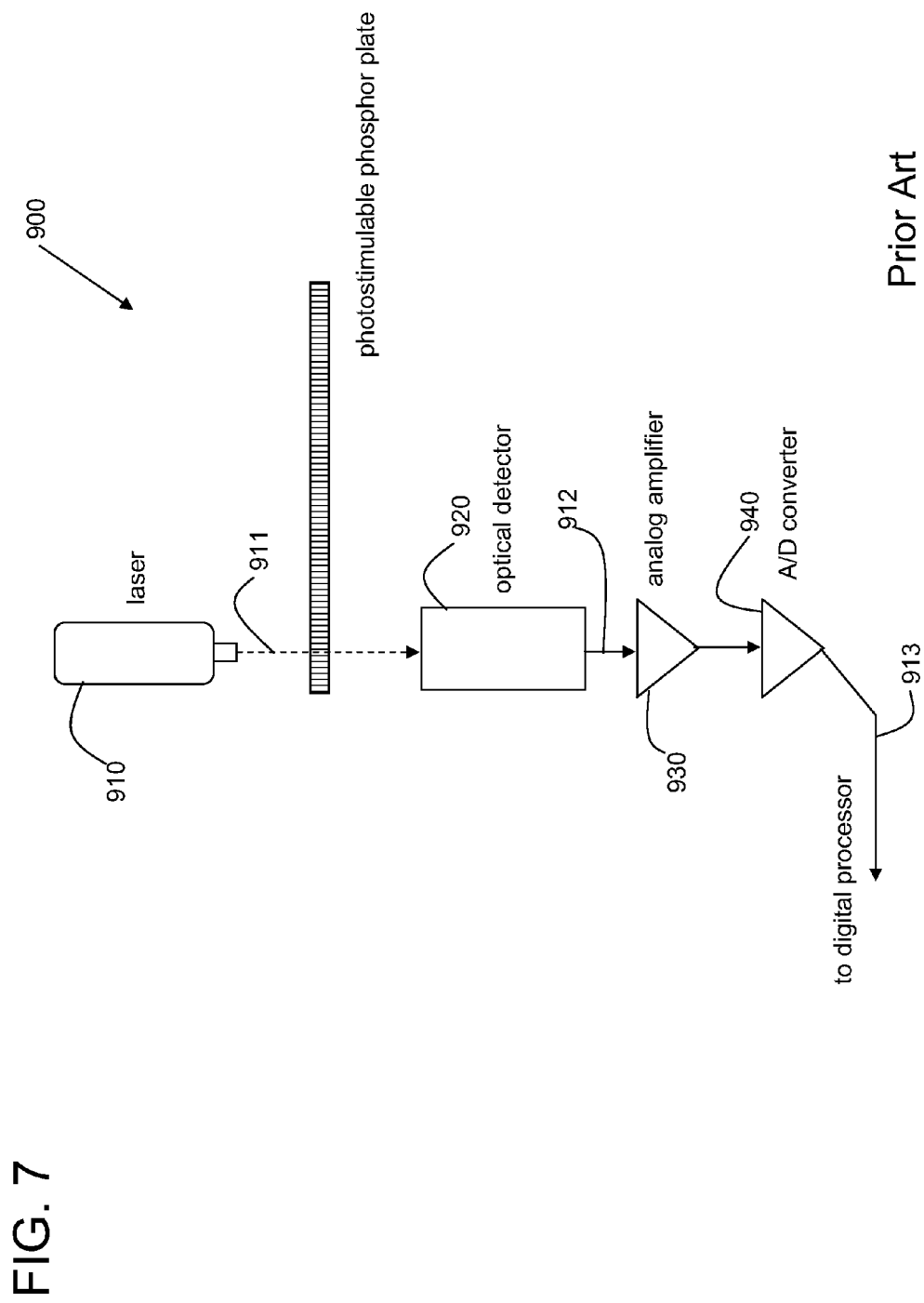
FIG. 7 illustrates a schematic block diagram of an example embodiment of the code reading device of FIG. 2 as being an optical reader, and an example embodiment of a process for reading the optical code of the X-ray sensitive phosphor plate of FIG. 6.

FIG. 7 illustrates a schematic block diagram of an example embodiment of the code reading device 320 of FIG. 2 as being an optical reader 900, and an example embodiment of a process for reading the optical code 810 of the X-ray sensitive phosphor plate 800 of FIG. 6. The optical reader 900 includes a laser source 910 which is used to scan the open and filled holes forming the optical code 810 of the X-ray sensitive phosphor plate 800.

The optical reader 900 also includes an optical detector 920. When scanning the optical code 810 of an X-ray sensitive phosphor plate placed in the scanning apparatus 250, a laser beam 911 emitted from the laser source 910 passes through a hole of the code 810 and is received at the optical detector 920, representing a digital "1" of the code 810. When the laser beam 911 scans over a filled hole, the optical detector 920 does not receive the laser beam 911, representing a digital "0" of the code 810. In this manner, the entire optical code 810 formed by the open and filled holes of the X-ray sensitive phosphor plate 800 may be read. The optical detector 920 converts the received light beam 911 (or lack thereof) to an analog electrical signal 912. The laser source may be mounted on a motor assembly which scans the laser beam 911 across the open and filled holes. Alternatively, a rotating mirror may be employed in a manner similar to that of FIG. 3.

The optical reader 900 includes an analog amplifier 930 operationally connected to an output of the optical detector 920 to receive the analog electrical signal 912 and amplify the analog electrical signal 912. The optical reader further includes an A/D converter 940 operationally connected to the output of the analog amplifier 930 to receive and convert the amplified analog electrical signal to a digital electrical signal 913. The digital electrical signals 913, corresponding to each of the open and filled holes of the optical code 810, may be forwarded to the digital processing and network transmitting apparatus 330 of the scanning apparatus 250 as the identifying code of the X-ray sensitive phosphor plate 800.

Figure 8:
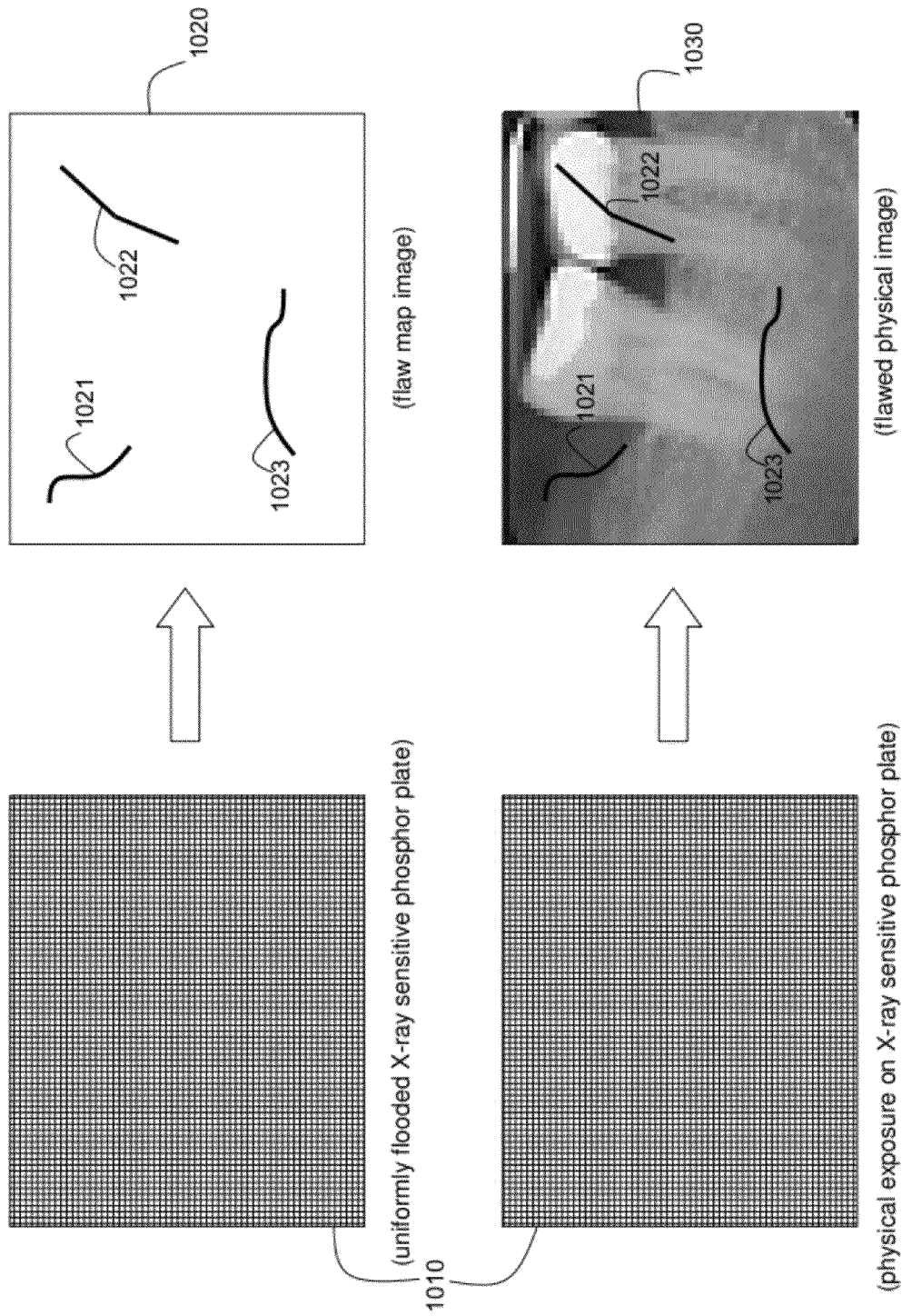
FIG. 8 illustrates an example embodiment of a process of generating flaw map image data using an X-ray sensitive phosphor plate, and an example embodiment of a process for generating physical image data using the X-ray sensitive phosphor plate.

FIG. 8 illustrates an example embodiment of a process of generating flaw map image data using an X-ray sensitive phosphor plate, and an example embodiment of a process for generating physical image data using the X-ray sensitive phosphor plate. Referring to FIG. 8, an X-ray sensitive phosphor plate 1010 has been uniformly flooded with X-ray radiation using an X-ray source (e.g., 110). As an option, a phantom plate may be placed between the X-ray source and the phosphor plate to provide a level of uniform attenuation or to project a known pattern onto the X-ray sensitive plate. By uniformly flooding the plate 1010 with X-ray radiation and subsequently scanning the plate 1010 with a laser scanner (e.g., 310) to read out image data, a resultant uniform image may theoretically be generated. In the uniform image, the values of all pixel data will theoretically be the same (or at least very nearly the same). However, if there are flaws (e.g., scratches 1021, 1022, 1023) on the plate 1010 that have damaged certain regions of the plate 1010, then those damaged regions may not properly respond to being radiated and subsequently scanned. As a result, the flaws (1021, 1022, 1023) may appear in the resultant image and the resultant image will constitute flaw map image data 1020.

The flaw map image data 1020 may be used to identify or find the flawed pixels in the image data. In the flaw map image data 1020, the vast majority of the pixel values will be the same (or at least very nearly the same). However, those pixels that correspond to damaged regions of the plate 1010 will have pixel values that deviate significantly from the majority of the pixels. As a result, a computer-based platform may be used to search the flaw map image data 1020 for such deviant or flawed pixel values and identify the associated flawed pixel locations using an image analysis algorithm on the computer-based platform. In accordance with an embodiment of the present invention, the raw flaw map image data 1020 may be digitally filtered (e.g., high-pass filtered) before searching for deviant pixels in order to enhance any flaws in the flaw map image data 1020, thus making it easier to find the flawed pixels. In accordance with an embodiment of the present invention, the image analysis algorithm computes a mean pixel value from all of the pixel values in the image 1020 and then identifies those individual pixel values which deviate from the mean pixel value by at least a predetermined amount or percentage, for example.

Once the flawed pixels are found and identified, the locations of the identified flawed pixels may be stored in the computer-based platform along with the flaw map image data 1020. Furthermore, an identifying code, which was read by a code reader (e.g., 320) when the plate 1010 was scanned, may be associated with the flaw map image data 1020 and with the identified flawed pixel locations within the computer-based platform.

Even though the plate 1010 may be damaged, the plate 1010 may subsequently be used to capture a physical representation of, for example, an anatomical portion (e.g., teeth) of a patient by exposing the plate 1010 to X-ray radiation from an X-ray source that has passed through the anatomical portion (e.g., as shown in FIG. 1). The plate 1010 may then be scanned with a laser scanner (e.g., 310) to read out the physical image, resulting in physical image data 1030 (see FIG. 8). The flawed physical image data 1030 may be stored in the computer-based platform along with the flaw map image data 1020. Furthermore, an identifying code, which was read by a code reader (e.g., 320) when the plate 1010 was again scanned, may be associated with the flawed physical image data 1030, which is the same identifying code that was read and stored previously when scanning the plate 1010 to produce the flaw map image data 1020.

However, the physical image data 1030 will not only include pixel values representing the exposed anatomical portion, but will also include damaged or flawed pixel values due to the scratches 1021, 1022, and 1023 on the plate 1010. The flawed pixels may degrade the physical image and possibly cause a user to misinterpret the image. For example, the scratch 1022 in the physical image may be incorrectly interpreted as a crack in a tooth. Therefore, it is desirable to eliminate, or at least minimize, the flaws in the physical image. This may be accomplished by applying image processing techniques to the physical image data 1030 using the flawed pixel information from the flaw map image data 1020.

Figure 10:
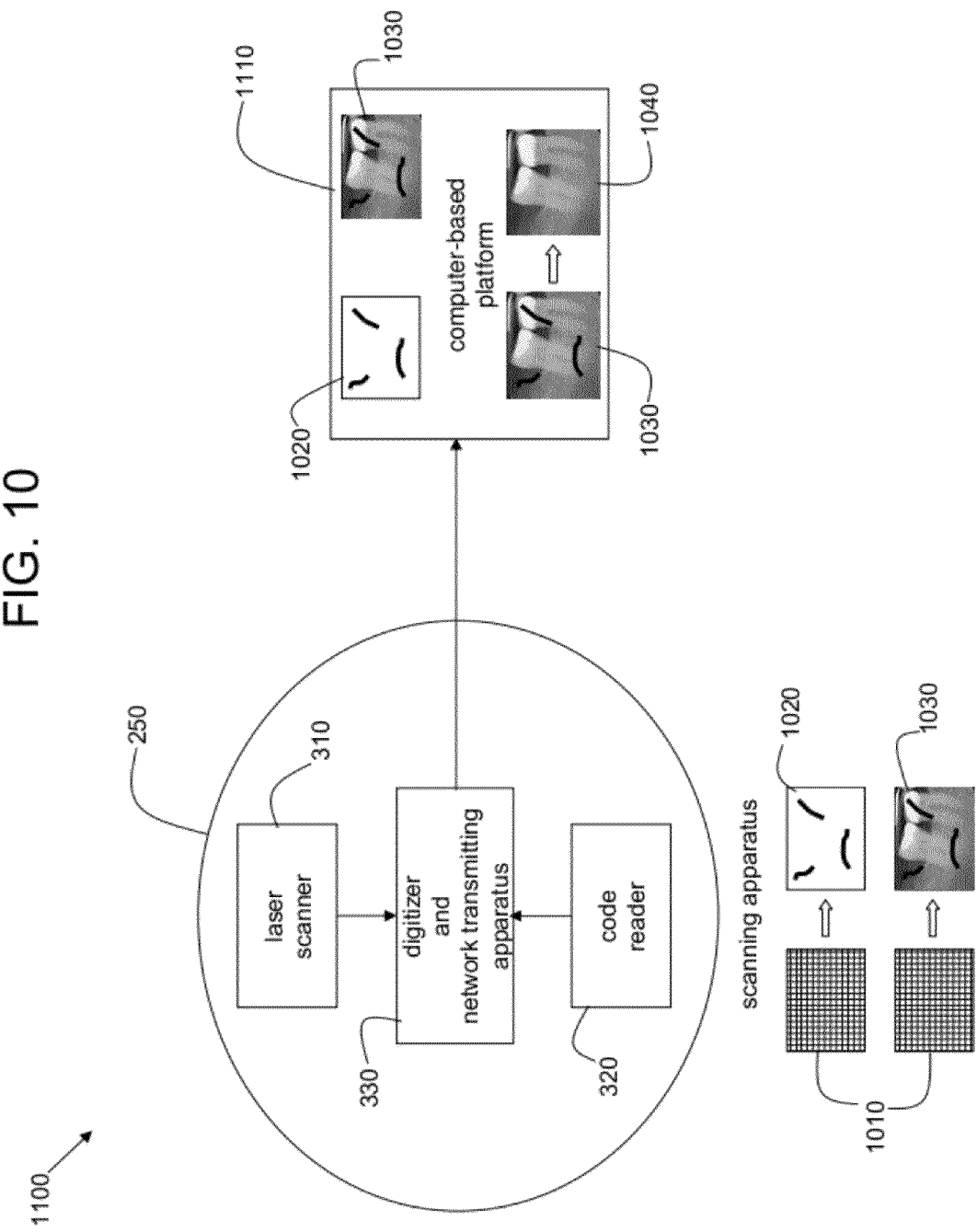
FIG. 10 illustrates an example embodiment of a system for generating a corrected physical image from flawed physical image data using the flaw map image data.

FIG. 9 illustrates an example embodiment of a process of generating a flawless or corrected physical image 1040 from flawed physical image data 1030 using the flaw map image data 1020. Furthermore, FIG. 10 illustrates an example embodiment of a system 1100 for generating a corrected physical image 1040 from flawed physical image data 1030 using the flaw map image data 1020. The system includes the scanning apparatus 250 and a computer-based platform 1110 operatively connected to the scanning apparatus 250. The computer-based platform 1110 may include a personal computer (PC) or a workstation, for example. Optionally, the computer-based platform may include an X-ray imaging machine, for example. Other types of computer-based platforms are possible as well, in accordance with various other embodiments of the present invention. Such computer-based platforms 1110 have at least one processor capable of executing software instructions.

In accordance with an embodiment of the present invention, the identified flawed pixel locations from the flaw map image data 1020 may be correlated to corresponding pixels locations within the flawed physical image data 1030. The computer-based platform 1110 may apply an image alignment algorithm to align the flaw map image data 1020 with the physical image data 1030. Those pixels in the physical image data 1030 that align with the identified flawed pixel locations in the flaw map image data 1020 are designated as correlated pixel locations in the physical image data 1030. Image alignment algorithms are well known in the art.

Figure 11:
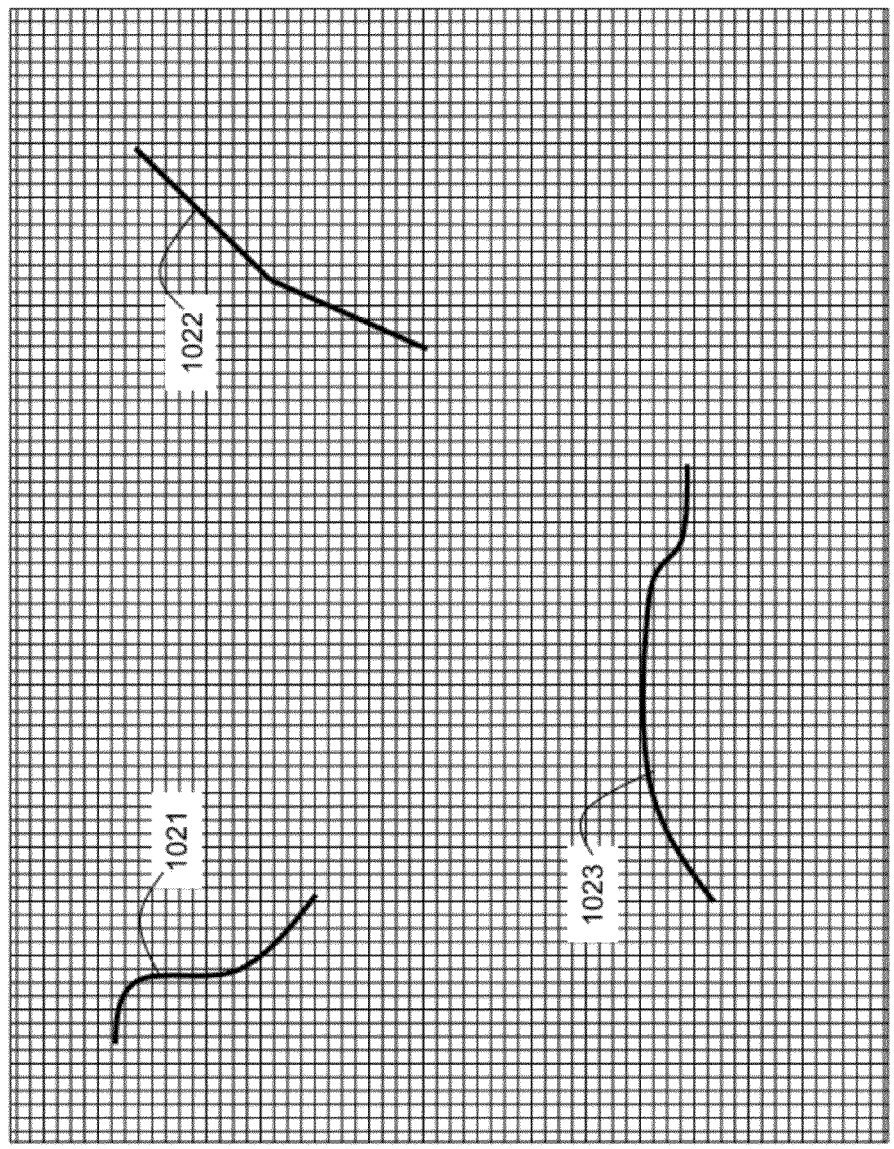
FIG. 11 illustrates image pixel locations having scratches running through particular flawed pixel locations.

For example, FIG. 11 illustrates image pixel locations having the scratches 1021, 1022, and 1023 running through particular flawed pixel locations. Each individual square represents a pixel location of the scanned plate 1010. When correlated to corresponding pixel locations in the physical image data 1030, an image processing algorithm may be applied to the physical image data 1030 to correct the correlated pixel locations in the physical image data 1030 to eliminate, or at least minimize the flaws.

Figure 12:
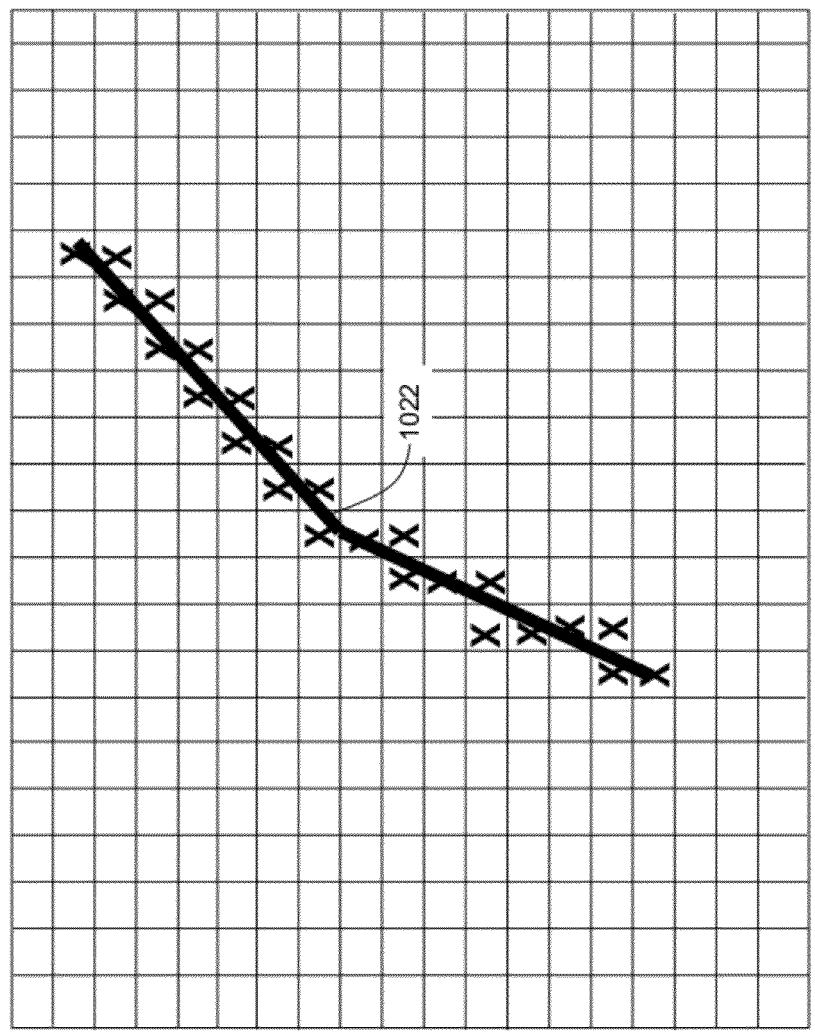
FIG. 12 illustrates a portion of the image pixel locations of FIG. 11 showing a particular scratch running through particular flawed pixel locations.
Figure 13:
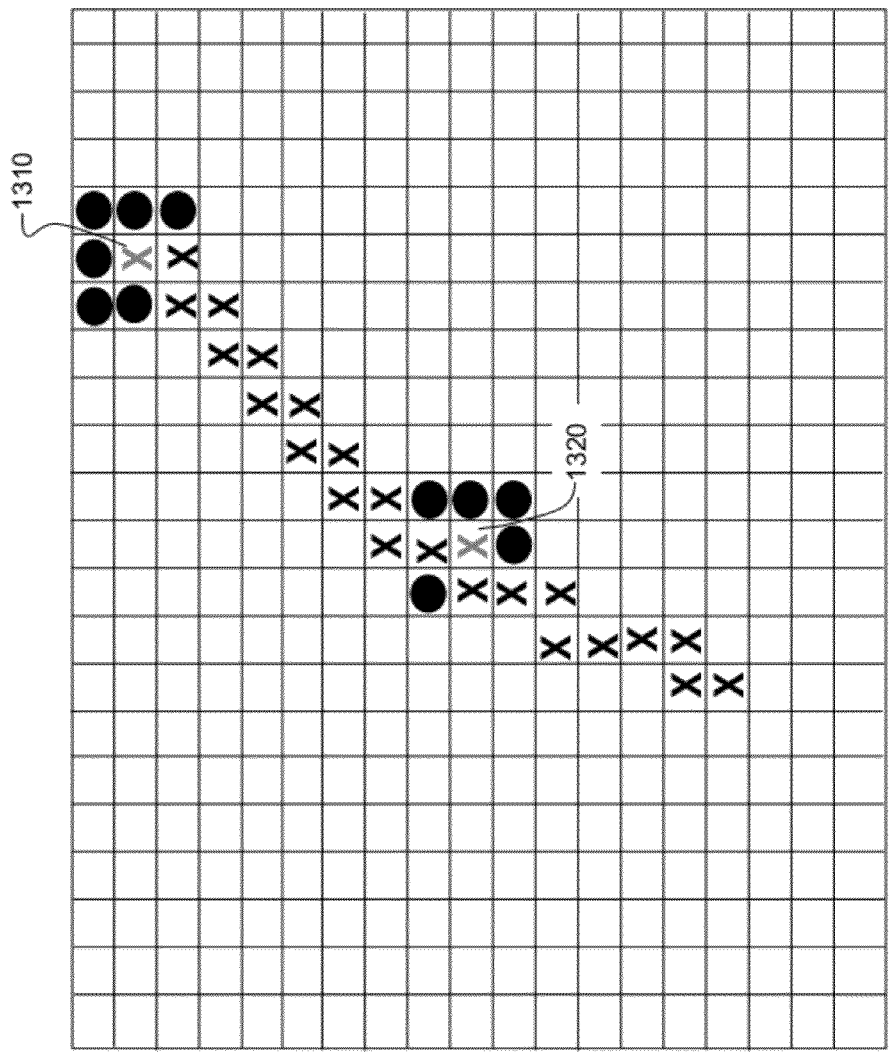
FIG. 13 shows the flawed pixel locations of FIG. 12 marked with an "X" and illustrates how two of the flawed pixel locations may be corrected.

In particular, FIG. 12 illustrates a portion of the image pixel locations of FIG. 11 showing the scratch 1022 running through particular flawed pixel locations. Those pixel locations that are affected by the scratch 1022 are marked with an "X" in FIG. 12 to clearly illustrate the flawed pixel locations. FIG. 13 shows the flawed pixel locations of FIG. 12 marked with an "X" and illustrates, as an example, how two of the flawed pixel locations may be corrected.

An example embodiment of an image processing algorithm for correcting flawed pixels in a flawed physical image uses a nearest neighbor technique. For example, referring to FIG. 13, the flawed pixel location 1310 is surrounded by six non-flawed nearest neighbor pixel locations (marked as black circles for illustration only) and two flawed nearest neighbor pixel locations (marked by X's for illustration only). The image processing algorithm computes an average value of the six non-flawed pixel locations and replaces the flawed pixel location under consideration 1310 with the computed average value.

Similarly, the flawed pixel location 1320 is surrounded by five non-flawed nearest neighbor pixel locations (marked as black circles for illustration only) and three flawed nearest neighbor pixel locations (marked by X's for illustration only). The image processing algorithm computes an average value of the five non-flawed pixel locations and replaces the flawed pixel location under consideration 1320 with the computed average value. Such a process may be repeated for each flawed pixel location in order to correct the values of the flawed pixel locations based on surrounding nearest neighbor non-flawed pixel locations. The result is a non-flawed or corrected physical image 1040.

The image processing algorithm may be more sophisticated than simply computing a simple average of nearest neighbor pixel values for each flawed pixel, in accordance with other embodiments of the present invention. For example, if the number of unflawed nearest neighbor pixel locations for a particular flawed pixel under consideration is only two, and the difference between the two pixel values is large (e.g., greater than some predefined difference threshold value), then the flawed pixel under consideration may simply be replaced with the larger (or smaller) pixel value of the two unflawed nearest neighbor pixel values. Such a direct replacement method can help to maintain sharp anatomical edges within an image.

As another example, if the number of unflawed nearest neighbor pixel locations for a particular flawed pixel under consideration is zero (i.e., the flawed pixel under consideration is totally surrounded by other flawed pixels), then the image processing algorithm may first correct the surrounding flawed pixel locations based on, for example, averaging as described above herein, and then correct the particular flawed pixel location under consideration using the surrounding corrected pixel locations. Other image processing algorithm correction scenarios are possible as well.

In this manner, only the identified flawed pixels are corrected. The non-flawed pixel locations are left intact. Such a process may allow a damaged (e.g., scratched) X-ray sensitive phosphor plate to continue to be used for an extended period of time. Periodically, the flaw map image for a particular X-ray sensitive phosphor plate may be updated to account for any new damage (e.g., new scratches) that may have occurred to the plate. In this way, the useful life of the phosphor plate may be further extended. However, the amount of damage to a plate may reach a point where the damage is so extensive that it makes more sense to replace the plate than to continue to try to correct image defects.

The computer-based platform may include an algorithm for computing a percentage of the total number of pixels that are flawed for a particular plate using the flaw map image data for the plate. When the percentage of flawed pixels meets or exceeds a particular threshold value, then the computer-based platform may output a message to the user indicating that the plate should be replaced via a display of the computer-based platform. As an alternative, such an algorithm may be applied to individual sections of the plate (i.e., of the flawed map image data) and if the percent of flawed pixels in any one section exceeds a predetermined threshold, the computer-based platform may output a message to the user, via a display of the computer-based platform, indicating that the plate should be replaced. Furthermore, the computer-based platform may simply report to the user a level of degradation of the plate based on the percentage of flawed pixels, for example. Other approaches for determining when to replace a plate or how to report a level of degradation of the plate are possible as well, in accordance with other embodiments of the present invention. Also, the computer-based platform may keep track of the number of times that an X-ray sensitive phosphor plate is used to generate physical image data. After a predefined number of times is reached, the computer-based platform may indicate to the user, via a display of the computer-based platform, that the plate should be replaced soon.

In summary, a system, a method, and computer readable media for generating a corrected image from image information extracted from an X-ray sensitive phosphor plate are disclosed. First, flaw map image information is extracted from an X-ray sensitive phosphor plate in order to determine any flaws (e.g., scratches) on the plate. Then the plate is exposed to capture physical image information (e.g., anatomical information) and the physical image information is extracted from the plate. The flaw map information is used to identify corresponding flaws in the extracted physical image information. Image processing is performed to correct the flaws (e.g., due to scratches on the X-ray sensitive phosphor plate) in the physical image information to form a corrected physical image.

While the claimed subject matter of the present application has been described with reference to certain embodiments, it will be understood by those skilled in the art that various changes may be made and equivalents may be substituted without departing from the scope of the claimed subject matter. In addition, many modifications may be made to adapt a particular situation or material to the teachings of the claimed subject matter without departing from its scope. Therefore, it is intended that the claimed subject matter not be limited to the particular embodiment disclosed, but that the claimed subject matter will include all embodiments falling within the scope of the appended claims.

What is claimed is:

1. A method to generate a corrected image from image information extracted from an X-ray sensitive plate, said method comprising:
    generating flaw map image data using an X-ray sensitive phosphor plate;
    generating physical image data using said X-ray sensitive phosphor plate;
    identifying scratched pixel locations within said flaw map image data using a computer-based platform;
    correlating pixel locations within said physical image data with said identified scratched pixel locations within said flaw map image data using said computer-based platform; and
    correcting said correlated pixel locations within said physical image data using said computer-based platform to generate a corrected physical image.

2. The method of claim 1 wherein said generating flaw map image data using said X-ray sensitive phosphor plate includes:
    uniformly flooding said X-ray sensitive phosphor plate with X-ray radiation using an X-ray source;
    reading said X-ray sensitive phosphor plate using a scanning apparatus to extract said flaw map image data;
    reading an identifying code on said X-ray sensitive phosphor plate using a code reading device; and
    storing said flaw map image data in said computer-based platform and associating said flaw map image data with said identifying code within said computer-based platform.

3. The method of claim 2 wherein said identifying code is implemented on said X-ray sensitive phosphor plate via one of radio frequency identification (RFID) technology, optical encoding technology, magnetic encoding technology, and bar coding technology.

4. The method of claim 1 wherein said generating physical image data using said X-ray sensitive phosphor plate includes:
    capturing a physical representation on said X-ray sensitive phosphor plate using an X-ray source;
    reading said X-ray sensitive phosphor plate using a scanning apparatus to generate physical image data;
    reading an identifying code on said X-ray sensitive phosphor plate using a code reading device; and
    storing said physical image data in said computer-based platform and associating said physical image data with said identifying code within said computer-based platform.

5. The method of claim 4 wherein said identifying code is implemented on said X-ray sensitive phosphor plate via one of radio frequency identification (RFID) technology, optical encoding technology, magnetic encoding technology, and bar coding technology.

6. The method of claim 1 wherein said step of identifying scratched pixel locations within said flaw map image data includes applying an image analysis algorithm to said flaw map image data using said computer-based platform.

7. The method of claim 1 wherein said step of correlating pixel locations within said physical image data with said identified scratched pixel locations within said flaw map image data includes applying an image alignment algorithm to align said flaw map image data with said physical image data using said computer-based platform.

8. The method of claim 1 wherein said step of correcting said correlated pixel locations within said physical image data to generate a corrected physical image includes applying an image processing algorithm to said physical image data using said computer-based platform.

9. The method of claim 1 further comprising reporting a level of degradation of said X-ray sensitive phosphor plate based on said identified scratched pixel locations using said computer-based platform.

10. The method of claim 1 further comprising tracking a number of times that said X-ray sensitive phosphor plate is used to generate said physical image data using said computer-based platform.

11. The method of claim 1 wherein said generating flaw map image data using said X-ray sensitive phosphor plate includes:
    uniformly flooding said X-ray sensitive phosphor plate with X-ray radiation using an X-ray source;
    reading said X-ray sensitive phosphor plate using a scanning apparatus to extract said flaw map image data; and
    storing said flaw map image data in a memory of said X-ray sensitive phosphor plate.

12. The method of claim 1 wherein said generating physical image data using said X-ray sensitive phosphor plate includes:
    capturing a physical representation on said X-ray sensitive phosphor plate using an X-ray source;
    reading said X-ray sensitive phosphor plate using a scanning apparatus to generate physical image data;
    reading a memory of said X-ray sensitive phosphor plate using a memory reading device to read said flaw map image data; and
    storing said physical image data and said flaw map image data in said computer-based platform and associating said physical image data with said flaw map image data within said computer-based platform.

13. The method of claim 1 wherein said generating flaw map image data using said X-ray sensitive phosphor plate includes:
    exposing said X-ray sensitive phosphor plate to X-ray radiation through an attenuating phantom plate using an X-ray source;
    reading said X-ray sensitive phosphor plate using a scanning apparatus to extract said flaw map image data;
    reading an identifying code on said X-ray sensitive phosphor plate using a code reading device; and
    storing said flaw map image data in said computer-based platform and associating said flaw map image data with said identifying code within said computer-based platform.

14. The method of claim 1 wherein said generating flaw map image data using said X-ray sensitive phosphor plate includes:
    exposing said X-ray sensitive phosphor plate to X-ray radiation through an attenuating phantom plate using an X-ray source;
    reading said X-ray sensitive phosphor plate using a scanning apparatus to extract said flaw map image data; and
    storing said flaw map image data in a memory of said X-ray sensitive phosphor plate.

15. A system to generate a corrected image from image information extracted from an X-ray sensitive plate, said system comprising:
    means for generating flaw map image data using an X-ray sensitive phosphor plate;
    means for generating physical image data using said X-ray sensitive phosphor plate;

means for identifying scratched pixel locations within said flaw map image data;

means for correlating pixel locations within said physical image data with said identified scratched pixel locations within said flaw map image data; and means for correcting said correlated pixel locations within said physical image data to generate a corrected physical image.

16. The system of claim 15 wherein said means for generating flaw map image data using an X-ray sensitive plate includes:

means for uniformly flooding said X-ray sensitive phosphor plate with X-ray radiation;

means for reading said X-ray sensitive phosphor plate to extract said flaw map image data;

means for reading an identifying code on said X-ray sensitive phosphor plate; and means for storing said flaw map image data and associating said flaw map image data with said identifying code.

17. The system of claim 16 wherein said identifying code is implemented on said X-ray sensitive phosphor plate via one of radio frequency identification (RFID) means, optical encoding means, magnetic encoding means, and bar coding means.

18. The system of claim 15 wherein said means for generating physical image data using said X-ray sensitive plate includes:

means for capturing a physical representation on said X-ray sensitive phosphor plate;

means for reading said X-ray sensitive phosphor plate to generate physical image data;

means for reading an identifying code on said X-ray sensitive phosphor plate; and means for storing said physical image data and associating said physical image data with said identifying code.

19. The system of claim 18 wherein said identifying code is implemented on said X-ray sensitive phosphor plate via one of radio frequency identification (RFID) means, optical encoding means, magnetic encoding means, and bar coding means.

20. The system of claim 15 wherein said means for identifying scratched pixel locations within said flaw map image data includes means for performing image analysis on said flaw map image data.

21. The system of claim 15 wherein said means for correlating pixel locations within said physical image data with said identified scratched pixel locations within said flaw map image data includes means for aligning said flaw map image data with said physical image data.

22. The system of claim 15 wherein said means for correcting said correlated pixel locations within said physical image data to generate a corrected physical image includes means for image processing said physical image data.

23. The system of claim 15 further comprising means for reporting a level of degradation of said X-ray sensitive phosphor plate based on said identified scratched pixel locations.

24. The system of claim 15 further comprising means for tracking a number of times that said X-ray sensitive phosphor plate is used to generate said physical image data.

25. Non-transitory computer readable media having computer readable instructions recorded thereon for generating a corrected image from image information extracted from an X-ray sensitive plate, said instructions comprising:

instructions for identifying scratched pixel locations within flaw map image data extracted from an X-ray sensitive phosphor plate;

instructions for correlating pixel locations within physical image data extracted from said X-ray sensitive phosphor plate with said identified scratched pixel locations within said flaw map image data; and instructions for correcting said correlated pixel locations within said physical image data to generate a corrected physical image.

26. The non-transitory computer readable media of claim 25 wherein said instructions for identifying scratched pixel locations within said flaw map image data include instructions for applying an image analysis algorithm to said flaw map image data.

27. The non-transitory computer readable media of claim 25 wherein said instructions for correlating pixel locations within said physical image data with said identified scratched pixel locations within said flaw map image data include instructions for applying an image alignment algorithm to align said flaw map image data with said physical image data.

28. The non-transitory computer readable media of claim 25 wherein said instructions for correcting said correlated pixel locations within said physical image data to generate a corrected physical image include instructions for applying an image processing algorithm to said physical image data.

29. The non-transitory computer readable media of claim 25 further comprising instructions for associating said flaw map image data with said physical image data based on a common identifying code.

30. The non-transitory computer readable media of claim 25 further comprising instructions for reporting a level of degradation of said X-ray sensitive phosphor plate based on said identified scratched pixel locations.

31. The non-transitory computer readable media of claim 25 further comprising instructions for tracking a number of times that said X-ray sensitive phosphor plate is used to generate said physical image data.

* * * * *